US009581553B2

(12) United States Patent
Pan

(10) Patent No.: US 9,581,553 B2
(45) Date of Patent: Feb. 28, 2017

(54) EXAMINATION METHOD FOR DISTINGUISHING BETWEEN NATURAL DIAMOND AND SYNTHETIC CVD/HPHT DIAMONDS

(71) Applicant: Dong-Shyogn Pan, Taipei (TW)

(72) Inventor: Dong-Shyogn Pan, Taipei (TW)

( * ) Notice: Subject to any disclaimer, the term of this patent is extended or adjusted under 35 U.S.C. 154(b) by 0 days.

(21) Appl. No.: 14/838,377

(22) Filed: Aug. 28, 2015

(65) Prior Publication Data
US 2016/0109374 A1    Apr. 21, 2016

Related U.S. Application Data

(60) Provisional application No. 62/065,617, filed on Oct. 18, 2014.

(51) Int. Cl.
*G01N 21/87* (2006.01)
*G01N 21/65* (2006.01)
*G01N 33/38* (2006.01)

(52) U.S. Cl.
CPC ............ *G01N 21/87* (2013.01); *G01N 21/65* (2013.01); *G01N 33/381* (2013.01)

(58) Field of Classification Search
CPC ....... G01N 21/87; G01N 33/381; G01N 21/65
See application file for complete search history.

(56) References Cited

U.S. PATENT DOCUMENTS

2006/0279732 A1* 12/2006 Wang ...................... G01J 3/02
356/326
2013/0188181 A1* 7/2013 Angel ...................... G01J 3/44
356/301
2016/0109373 A1* 4/2016 Pan ...................... G01N 21/87
356/30
2016/0178530 A1* 6/2016 Davies ................. G01N 21/87
209/578

FOREIGN PATENT DOCUMENTS

CN          101694544 A   *   4/2010

OTHER PUBLICATIONS

Renata Jasinevicius, "Characterization of Vibrational and Electronic Features in the Raman Spectra of Gem Minerals", Master of Science thesis, Department of Geosciences, The University of Arizona, 2009.*

* cited by examiner

*Primary Examiner* — Kara E Geisel
*Assistant Examiner* — Violeta A Prieto

(57) ABSTRACT

This invention is within the technical field of distinguishing between natural diamond and synthetic CVD and HPHT diamonds, involves an examination technique using the Raman spectra. Procedurally, a highly sensitive Raman spectrometer (S/N>10,000) is used to scan and examine the diamond sample. The spectrometer is fitted with a tailor-made probe that has a large facula and surface area. Specially developed software is then used to perform an intensity correction and a background elimination to obtain a specific Raman spectral range (250-2800 cm$^{-1}$) with the corrected intensity and a smooth baseline. Next, the Raman peak intensity of 2030 cm$^{-1}$ (the post-correction and -standardization characteristic peak) is used as a basis to distinguish between natural diamond and synthetic CVD and HPHT diamonds. This method has the advantages of being non-destructive, simple, fast, and practical identification for diamonds.

1 Claim, 5 Drawing Sheets

EXAMINATION METHOD FOR DISTINGUISHING BETWEEN NATURAL DIAMOND AND SYNTHETIC CVD/HPHT DIAMONDS

RELATED APPLICATIONS

This application claims priority benefit of U.S. Provisional Patent Application No. 62/065,617 filed 18 Oct. 2014, of which is hereby incorporated by reference.

BACKGROUND OF THE INVENTION

1. Field of the Invention

The present invention relates to a non-destructive examination method for distinguishing between natural diamond and synthetic CVD/HPHT diamonds is proposed, whereby a Raman characteristic peak is used to correct and standardize the signal intensity for the rapid detection of differentiation between natural diamond and synthetic CVD/HPHT diamonds.

2. Related Art

Due to technical improvements and reduce costs, there have been many high-quality synthetic diamonds on the market. Prices of synthetic and natural diamonds are highly unequal. The synthetic ones are available on the market at a price, which is about 40% less than natural diamond. There is still no scientific and effective method which can distinguish between natural and synthetic diamonds until now. How to effectively and correctly distinguish between natural and synthetic diamonds is an important technical method needs to be solved.

SUMMARY OF THE INVENTION

Accordingly, an object of the present invention is to provide quantitative data for the distinguishing between natural diamond and synthetic CVD and HPHT diamonds, the signal intensity of the characteristic peak of the Raman spectra (determined from the quantification of scientific data) is used as a rapid examination method for distinguishing between natural diamond and synthetic CVD and HPHT diamonds.

To achieve the above-mentioned object, the examination method for distinguishing between natural and synthetic CVD/HPHT diamonds, comprises: providing a Raman spectrometer having a laser beam of wavelength 785 nm and total laser energy of 450 mW for an average detection of diamond surfaces; three continuous scans being performed using a tailor-made probe having a large facula and surface area to obtain three spectra, from which an average Raman spectra is determined; defining a collection range of the spectrometer as 250-2800 $cm^{-1}$; and after the collection of the Raman spectral data, the intensity being subjected to two operations: (a) correction and standardization, and (b) background elimination that result in a Raman spectrogram with a smooth baseline and an calibrated intensity; wherein a carbon Raman characteristic peak for diamonds occurs at 1332 $cm^{-1}$, whereas natural diamonds have an extra nitrogen-derived Raman characteristic peak at 2030 $cm^{-1}$.

BRIEF DESCRIPTION OF THE DRAWINGS

FIG. 5 is a schematic chart illustrating Raman spectra of HPHT diamond specimens overlaid zoom in.

DESCRIPTION OF THE PREFERRED EMBODIMENTS

To provide quantitative data for the distinguishing between natural diamond and synthetic CVD and HPHT diamonds, the signal intensity of the characteristic peak of the Raman spectra (determined from the quantification of scientific data) is used as a rapid examination method for distinguishing between natural diamond and synthetic CVD and HPHT diamonds. The characteristic peak of the Raman spectra is used to correct and standardize the signal intensity for rapid examination. The procedures comprising the technique are detailed below.

Figure 1:
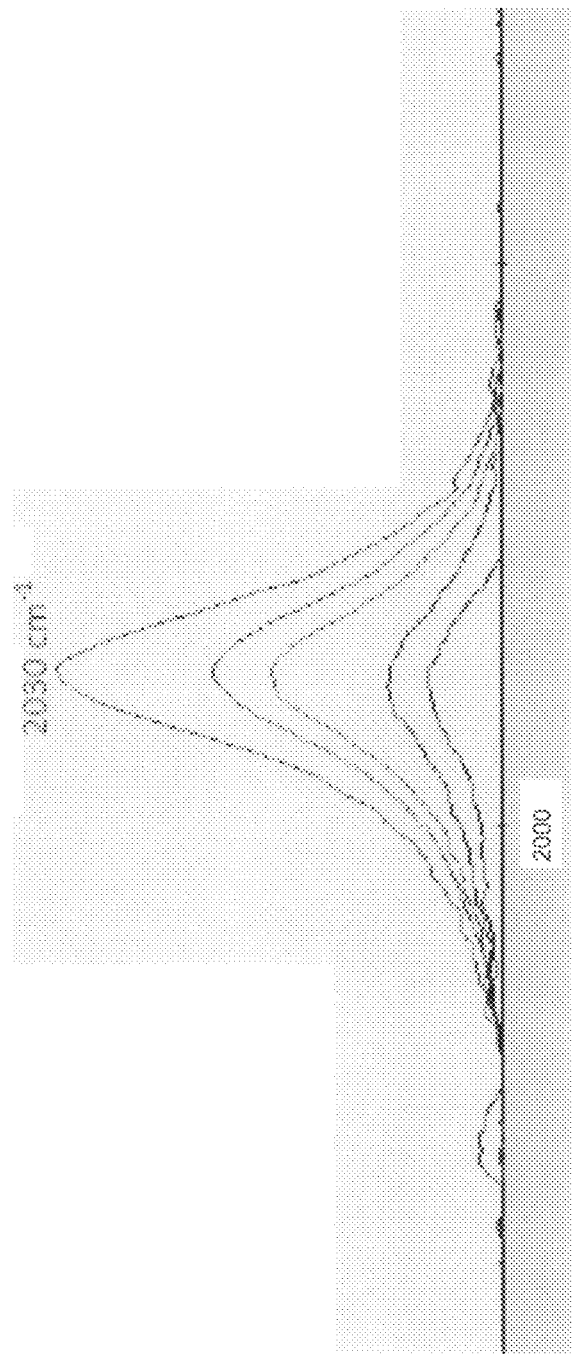
FIG. 1 is a schematic chart illustrating Raman spectra of natural diamonds at peak 2030 $cm^{-1}$.

Provides a Raman spectrometer having a laser beam of wavelength 785 nm and total laser energy of 450 mW for an average detection of diamond surfaces; three continuous scans being performed using a tailor-made probe having a large facula and surface area to obtain three spectra, from which an average Raman spectra is determined; defining a collection range of the spectrometer as 250-2800 $cm^{-1}$; and after the collection of the Raman spectral data, the intensity being subjected to two operations: (a) correction and standardization, and (b) background elimination that result in a Raman spectrogram with a smooth baseline and an calibrated intensity; wherein a carbon Raman characteristic peak for diamonds occurs at 1332 $cm^{-1}$, whereas natural diamonds have an extra nitrogen-derived Raman characteristic peak at 2030 $cm^{-1}$ (as shown in FIG. 1).

Figure 2:
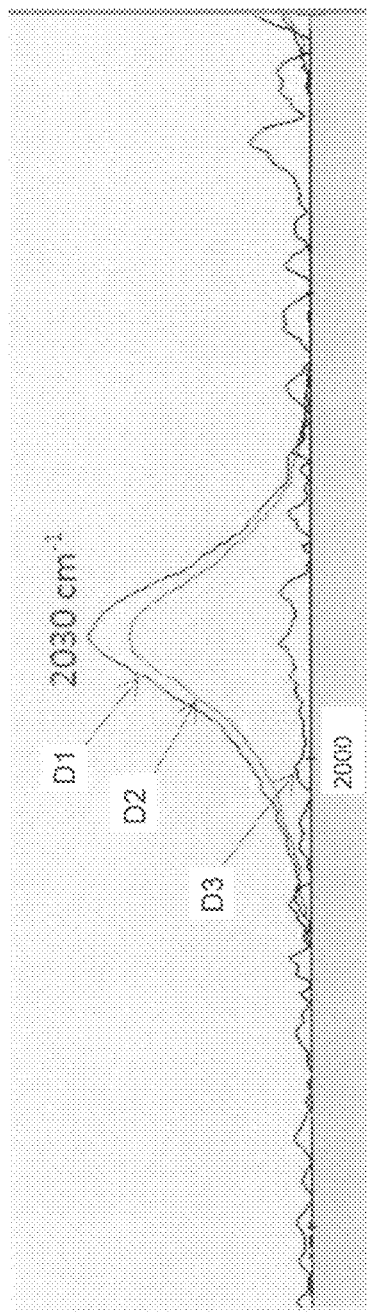
FIG. 2 is a schematic chart illustrating Raman spectra of natural CVD or HPHT diamond at peak 2030 $cm^{-1}$.

This Raman characteristic peak is not appeared in synthetic CVD and HPHT diamonds. Under the proposed method, the Raman spectra of natural diamonds D1 and D2, synthetic CVD diamonds, and synthetic HPHT diamonds samples D3 are collected (FIG. 2). The Raman peak at 2030 $cm^{-1}$ does not appear in the synthetic CVD and HPHT diamonds. Thus, it can be used as a basis to appraise whether the diamond is natural or synthetic one.

Figure 3:
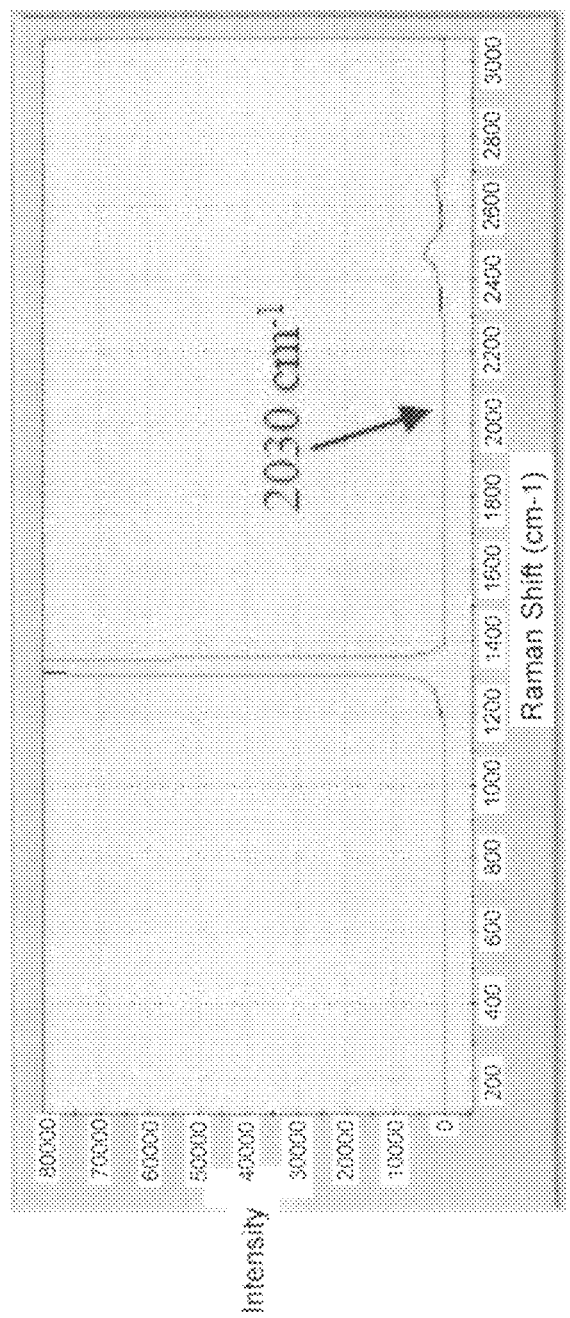
FIG. 3 is a schematic chart illustrating Raman spectra of CVD diamond at peak 2030 $cm^{-1}$.
Figure 4:
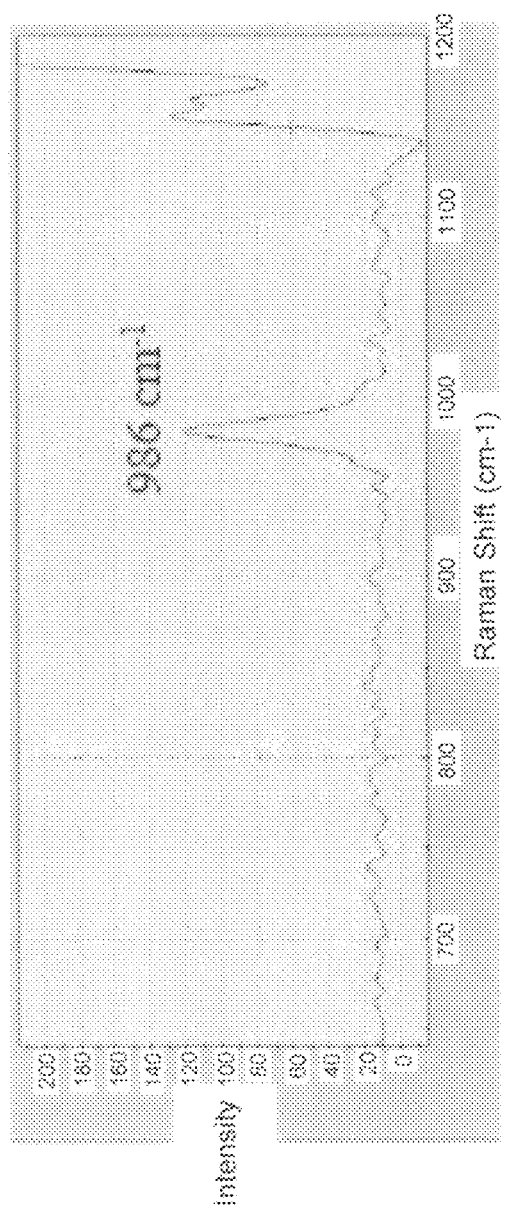
FIG. 4 is a schematic graphical zoom-in chart illustrating Raman spectra of CVD diamond at peak 986 $cm^{-1}$.

Generally the CVD type of synthetic diamonds do not contain nitrogen, thus as illustrated in FIG. 2, there are no trace of specific nitrogen-derived Raman peaks at 2030 $cm^{-1}$ under close examination. In FIGS. 3 and 4 under graphical zoom-in, a Raman peak at 986 $cm^{-1}$ can be observed, which is common across all CVD diamonds from the impurity (Si-derived) used in the manufacturing process. The trace of this impurity is so minute that this peak response is only observed under the most highly sensitive Raman analyzers as overtone spectrum.

Figure 5:
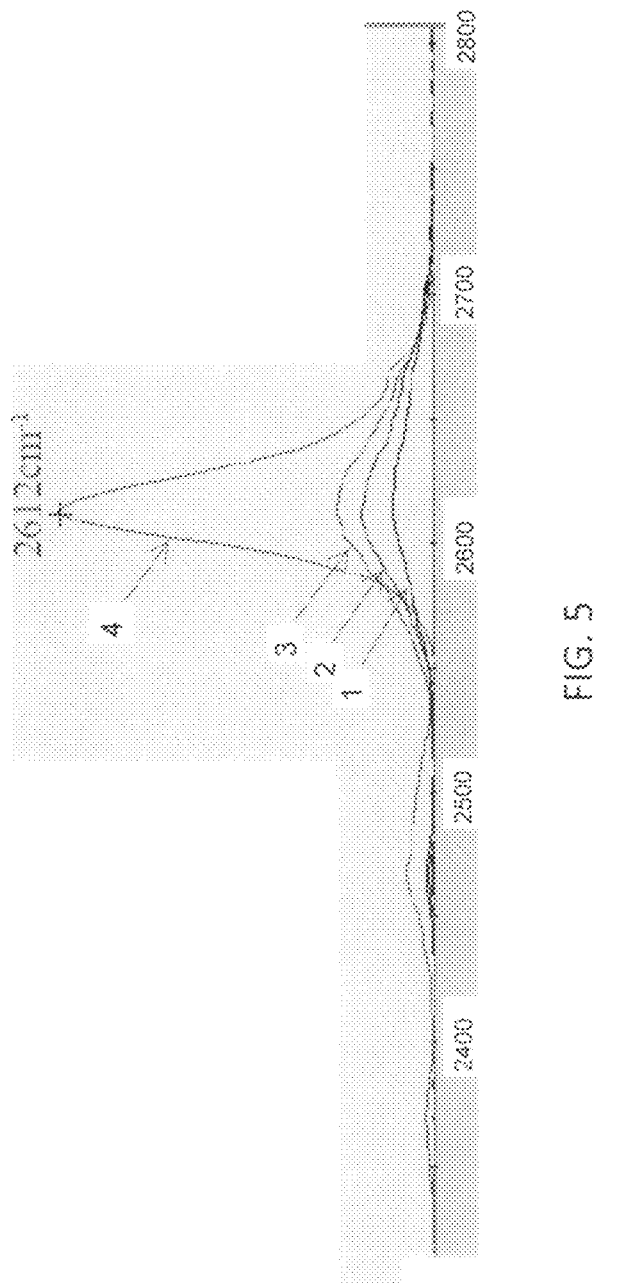

Moreover, another Raman peak at 2612 $cm^{-1}$ is specific to the HPHT diamonds (as shown in FIG. 5), which can lead into the hypothetical analysis that this is the result of diamond lattice displacement or distortion under high-pressure and high-temperature to give another peak response at Raman diamond second order.

However, the existence of the 2612 $cm^{-1}$ Rama peak is confirmed for HPHT samples, and specifically for rapid identification of the HPHT diamonds by using a high performance Raman analyzer. From FIG. 5, the Raman response from four samples of HPHT diamonds 1, 2, 3 and 4 are overlaid to present the different intensity of 2612 $cm^{-1}$ peak from different HPHT specimen.

The use of the Raman spectra in the proposed method has the following advantages: it is non-destructive, there is no requirement for pre-processing, it allows a rapid analysis, and it is based on scientific quantification. The main features of the proposed method are as follows:

(a) After the correction and standardization, from this method, by using a highly sensitive Raman analyzer, two indicative results can be deduced to detect CVD diamonds:
1. Raman peak at 986 $cm^{-1}$—exists as overtone spectrum from impurity (Si-derived).
2. Raman peak at 2030 $cm^{-1}$—CVD diamond does NOT produce response at this wave number, as opposed to natural diamonds that contains nitrogen-derived.

(b) After the correction and standardization, from this method, by using a highly sensitive Raman analyzer, two indicative results can be deduced to detect HPHT diamonds:
1. Raman peak at 2612 $cm^{-1}$—exists as the result of diamond lattice displacement or distortion under high-pressure and high-temperature to give another peak response at Raman diamond second order.
2. Raman peak at 2030 $cm^{-1}$—HPHT diamond does NOT produce response at this wave number, as opposed to natural diamonds that contains nitrogen-derived.

(c) This method can be applied for both loose and inlaid diamonds and for diamonds of all sizes.

(d) Specially developed software and standard samples are used to perform the correction and standardization, as well as the baseline processing. This reduces the slight differences in the intensities of the Raman peaks of the diamonds between analyses, thereby ensuring data consistency for each analysis.

It is understood that the invention may be embodied in other forms within the scope of the claims. Thus the present examples and embodiments are to be considered in all respects as illustrative, and not restrictive, of the invention defined by the claims.

What is claimed is:

1. An examination method for distinguishing between natural and synthetic CVD/HPHT diamonds, comprising:
   providing a Raman spectrometer having a laser beam of wavelength 785 nm and total laser energy of 450 mW for an average detection of diamond surfaces;
   three continuous scans being performed using a tailor-made probe having a large facula and surface area to obtain three spectra, from which an average Raman spectra is determined;
   defining a collection range of the spectrometer as 250-2800 $cm^{-1}$; and
   after the collection of the Raman spectral data, the intensity being subjected to two operations: (a) correction and standardization, and (b) background elimination that result in a Raman spectrogram with a smooth baseline and a calibrated intensity;
   wherein a carbon Raman characteristic peak for diamonds occurs at 1332 $cm^{-1}$, whereas natural diamonds have an extra nitrogen-derived Raman characteristic peak at 2030 $cm^{-1}$.

* * * * *